(12) United States Patent
Atabekov et al.

(10) Patent No.: US 6,933,378 B2
(45) Date of Patent: *Aug. 23, 2005

(54) METHODS FOR COEXPRESSION OF MORE THAN ONE GENE IN EUKARYOTIC CELLS

(76) Inventors: Joseph Atabekov, Lomonosovski prospekt 15-142, Moscow 117311 (RU); Timo Korpela, Kasarminkatu 5 as 8, FIN-20500 Turku (FI); Yurii Dorokhov, Profsojuznaja Street 146-3-187, Moscow 117321 (RU); Peter Ivanov, Vavilova Street 37A-18, Moscow 117312 (RU); Maxim Skulachev, Moscow State University, M-176, Moscow 117234 (RU); Nina Rodionova, Ramenski Street 19-184, Moscow 117607 (RU); Olga Karpova, Garibaldy Street 15-1-50, Moscow 117335 (RU)

( * ) Notice: Subject to any disclaimer, the term of this patent is extended or adjusted under 35 U.S.C. 154(b) by 0 days.

This patent is subject to a terminal disclaimer.

(21) Appl. No.: 09/911,732

(22) Filed: Jul. 25, 2001

(65) Prior Publication Data

US 2002/0034814 A1 Mar. 21, 2002

Related U.S. Application Data

(63) Continuation-in-part of application No. 09/424,793, filed as application No. PCT/FI98/00457 on May 29, 1998, now Pat. No. 6,376,745.

(30) Foreign Application Priority Data

May 30, 1997 (FI) .................................................. 972293

(51) Int. Cl.[7] .......................... C07H 21/04; C12P 21/06
(52) U.S. Cl. ....................... 536/24.1; 536/23.1; 435/41; 435/69.1
(58) Field of Search ...................... 435/41, 69.1, 320.1; 536/23.1

(56) References Cited

U.S. PATENT DOCUMENTS 6,376,745 B1 * 4/2002 Atabekov et al. ......... 73/861.03

FOREIGN PATENT DOCUMENTS

| EP | 0672754 | 9/1995 |
|----|---------|--------|
| GB | 2262099 | 6/1993 |
| WO | 9514775 | 6/1995 |
| WO | 9612028 | 4/1996 |
| WO | 96 27676 | 9/1996 |
| WO | 9633272 | 10/1996 |
| WO | 97 14809 | 4/1997 |

OTHER PUBLICATIONS

Thomas et al. Cowpea Mosaic virus Middle Component RNA Contains a Sequence that allow internal binding of ribosomes an that requires eukaryotic initiation factor 4F for optimal translation Journal of virology vol. 65 No. 6 Jun. 1991, pp. 2953–2959.*
Urwin et al. Functional characterization of the EMCV IRES in plants. Plant Journal vol. 24 No. 5, 2000, pp. 583–589.*
Bio/Technology, vol. 12, Jul. 1994, Yoshikazu Sugimoto et al., p. 694–p. 698.
Virology, vol. 232, 1997, P.A. Ivanov et al., p. 32–p. 43.
Journal of General Virology, vol. 75, 1994, Johnny Basso et al., pp. 3157–p. 3165.
Nucleic Acids Research, vol. 19, No. 16, 1991, Randal J. Kaufmann et al., p. 4485–p. 4490.
V. Gurtu et al., Biochem. and Biophys. Res. Comm., vol. 229, pp. 295–298 (1996) (Article No. 1795).
Kaminski and Jackson (1995) RNA 1:985–1000.
Thomas et al (1991) Journal of Virology 65:2953–2959.
Belsham et al (1991) Gen Virol 72:3109–3113.
Aran et al (1994) Proc Nat'l Acad Sci, USA 91:3176–3180.

* cited by examiner

*Primary Examiner*—James Ketter
*Assistant Examiner*—David Lambertson
(74) *Attorney, Agent, or Firm*—Birch, Stewart, Kolasch & Birch, LLP

(57) ABSTRACT

A primary object of this invention is to provide a method which will enable to coexpress simultaneously two (or more) desired genes in plant, animal or yeast cells, in transgenic plants and animals, or in vitro, in plant cell-derived or animal cell-derived translation systems. This objection is to be accomplished by utilizing sequence elements derived from RNAs of a tobamovirus upstream of MP gene or CP gene termed here as $IRES_{MP}$ and $IRES_{CP}$, respectively. The method of this invention involves the construction of a recombinant nucleic acid sequence which comprises a specific transcriptional promoter, a first gene expressible in eukaryotic cells linked to said transcriptional promoter, $IRES_{MP}$ or $IRES_{CP}$ located 3' to the first gene and a second gene expressible in eukaryotic cells, located 3' to IRES sequence such that the second gene is placed under the transcriptional control of IRES sequence originated from tobamovirus genome. The primary chimeric RNA transcript in positive sense polarity is produced by the transformed cells from the said promoter. The expression of the first gene occurs by direct translation whereas the translation of the 5'-distal gene(s) of bicistronic (or polycistronic) mRNA will be promoted by $IRES_{MP}$ or $IRES_{CP}$.

15 Claims, 13 Drawing Sheets

TMV U1

CrTMV

IRESmp,228CR dG = -59.5 [initially -58.9]   01Jul13-05-49-46 dG = -70 [initially -70.2]  01Jul13-06-19-02   IRESmp,228U dG = -14.6 [initially -14.6]   IRESmp75UI RESmp,228CGMMV dG = -58.14 [initially -63.1]  01Jul13-06-30-00 ived from Russian Academy of Sciences 332: 518–522; Dorokhov et al. (1994) FEBS Lett. 350: 5–8). A peculiar feature of crTMV is its ability to infect systemically the members of Cruciferae family. The crTMV RNA contains four ORFs encoding the proteins of 122 K (ORF1), 178 K (ORF2), the readthrough product of 122 K, 30 K MP. (ORF3) and 17 K CP (ORF4). Unlike other tobamoviruses, the coding regions of the MP and CP genes of crTMV overlap for 25 codons, i.e. 5' of the CP coding region are sequences encoding MP.

METHODS FOR COEXPRESSION OF MORE THAN ONE GENE IN EUKARYOTIC CELLS

This application is a continuation-in-part of Appln. Ser. No. 09/424,793 filed on Dec. 16, 1999 now U.S. Pat. No. 6,376,745, Which is the national stage application of PCT international application No. PCT/FI98/00457 which has an international filing date of May 29, 1998 which designated the United States, the entire contents of which are hereby incorporated by reference.

FIELD OF THE INVENTION

This invention relates to plant molecular biology and biotechnology and, in particular, to nucleic acid sequences which can mediate an internal and 3'-proximal gene expression from bi- and polycistronic mRNA transcripts in eukaryotic cells and in vitro in cell-free protein synthesizing systems. This invention will enable the expression of two or more transgenes in eukaryotic cells through the generation of bi- and polycistronic fusion mRNAs in which all the genes are translationally active due to the presence of the intercistronic IRES elements derived from a tobamovirus.

BACKGROUND OF THE INVENTION

According to the ribosome scanning model, traditional for most eukaryotic mRNAs, the 40S ribosomal subunit binds to the 5'-cap and moves along the nontranslated 5'-sequence until it reaches an AUG codon (Kozak (1986) Adv. Virus Res. 31: 229–292; Kozak (1989) J. Mol. Biol. 108: 229–241). Although for the majority of eukaryotic mRNAs only the first open reading frame (ORF) is translationally active, there are different mechanisms by which mRNA may function polycistronically (Kozak (1986) Adv. Virus Res. 31: 229–292). If the first AUG has unfavourable sequence context, 40S subunits may bypass it and initiate at downstream AUG codon (leaky scanning mechanism). Termination-reinitiation has also been suggested to explain the initiation of translation of functionally dicistronic eukaryotic mRNAs (Kozak (1989) J. Mol. Biol. 108: 229–241). Another mechanism for discontinuous ribosome migration ("shunting") on mRNA has been recently proposed for cauliflower mosaic virus (CaMV) 35S RNA (Futerrer et al. (1993) Cell 73: 789–802).

In contrast to the majority of eukaryotic mRNAs, the initiation of translation of picornaviral RNAs takes place by an alternative mechanism of internal ribosome entry. A picornaviral 5'-nontranslated region (5'NTR) contains a so-called internal ribosome entry site (IRES) or ribosome landing pad (Pelletier and Sonenberg (1988) Nature 334: 320–325; Molla et al. (1992) Nature 356: 255–257) which is folded into a complex secondary structure and contains a pyrimidine-rich tract followed by an AUG codon (Agol (1991) Adv. Virus Res. 40: 103–180; Wimmer et al. (1993) Annu. Rev. Genet.27: 353–436; Sonennberg and Pelletier (1989) BioEssays 11: 128–132). Internal ribosome entry has also been reported for other viral (Le et al. (1994) Virology 198: 405–411; Gramstat et al. (1994) Nucleic Acid Res. 22: 3911–3917) and cellular (Oh et al. (1992) Gen Dev. 6: 1643–1653) RNAs.

It is important to emphasize that the picornaviral and other known IRESes are not active in plant cell systems.

The genome of tobamoviruses (TMV UI is the type member of a group)) contains four large ORFs. In vitro translational experiments have shown that the two components of the replicase (the 130K and its read-through 183K proteins) are translated directly from the genomic RNA (Pelham and Jackson (1976) Eur. J. Biochem 67: 247–256). The other two proteins (30K movement protein, MP, and coat protein, CP) are translated from two individual subgenomic RNAs (sgRNAs). The structurally dicistronic I₂ sgRNA is translated to give the 30 K MP, while its 3'-terminal CP gene is silent and a monocistronic sgRNA codes the CP (Palukaitis and Zaitlin (1986) in The Plant Viruses, eds. Van Regenmortel and M. Fraenkel-Conrat, 2: 105–131, Plenum Press).

Recently a new tobarnovirus, crTMV, has been isolated from *Olearacia officinalis* L. plants and the crTMV genome has been sequenced (6312 nucleotides) (Dorokhov et al. (1993) Doklady of Russian Academy of Sciences 332: 518–522; Dorokhov et al. (1994) FEBS Lett. 350: 5–8). A peculiar feature of crTMV is its ability to infect systemically the members of Cruciferae family. The crTMV RNA contains four ORFs encoding the proteins of 122 K (ORF1), 178 K (ORF2), the readthrough product of 122 K, 30 K MP. (ORF3) and 17 K CP (ORF4). Unlike other tobamoviruses, the coding regions of the MP and CP genes of crTMV overlap for 25 codons, i.e. 5' of the CP coding region are sequences encoding MP.

We have reported recently that translation of the 3'-proximal CP gene of crTMV RNA occurs in vitro and in planta by a mechanism of internal ribosome entry which is mediated by a specific sequence element, $IRES_{CP}$ (Ivanov et al. (1997) Virology 232: 32–43).

Our results indicated that the 148-nt region upstream of the CP gene of crTMV RNA contained $IRES_{CP,148}^{CR}$ promoting internal initiation of translation in vitro. Dicistronic $IRES_{CP,148}^{CR}$ containing chimeric mRNAs with the 5'-terminal stem-loop structure preventing translation of the first gene, expressed the CP or β-glucuronidase (GUS) genes despite their 3'-proximal localization. The capacity of crTMV $IRES_{CP}$ for mediating internal translation in vitro distinguishes this tobamovirus from the well known type member of the genus, the TMV UI. However, in the present invention we show that the 148-nt sequence upstream from CP gene of TMV UI is capable of expressing moderately the 3'-proximal gene from dicistronic construct in transformed yeast cells, i.e. this sequence can be termed $IRES_{CP}^{UI}$. We found that the 75–228-nt region upstream of the MP gene of crTMV, TMV UI and cucumber green mottle mosaic virus contains IRESes that allow 5'-end-independent internal initiation of translation on dicistronic mRNAs containing IRES as the intercistronic spacer.

The present invention shows that genomes of tobamoviruses contain the IRES-elements upstream of both genes: the MP and CP genes capable of promoting the 3'-proximal gene expression from bicistronic mRNAs. Therefore, this invention relates to a novel functional activity of nucleotide sequences located upstream of the MP and/or CP genes of tobamoviruses: their ability to mediate the cap-independent expression of the 5'-distal genes being inserted as an intercistronic spacers in bi- (or polycistronic) eukaryotic mRNAs.

The tobamoviruses provide new examples of internal ribosome entry sites which are markedly distinct from IRESes shown for picornaviruses and other viral and eukaryotic mRNAs. The tobamovirus IRESes described in this invention are the first IRES sequences functional in plant cells described so far. In addition, the tobamovirus genome-derived IRES elements were shown to be functional in animal and yeast cells.

SUMMARY OF THE INVENTION

A primary object of this invention is to provide a method which will enable to express simultaneously two or more desired genes in transfected and/or transformed eukaryotic cells including plant, animal, human and yeast cells, and also transgenic plants and animals as well as in cell-free translation systems derived from eukaryotic cells. This objective is to be accomplished by utilizing RNA sequences from a tobamovirus genome upstream of the tobamovirus MP or CP gene that will be used as intercistronic spacers in bicistronic (or polycistronic) constructs. The method of this invention involves the construction of recombinant nucleic acid molecule which comprises a transcriptional promoter, a first structural gene expressible in eukaryotic cells linked to said transcriptional promoter, a nucleotide sequence upstream of the MP gene or the CP gene of a tobamovirus RNA referred to as $IRES_{MP}$ and $IRES_{CP}$, respectively, located 3' to the first gene, and a second structural gene expressible in eukaryotic cells, located 3' to $IRES_{MP}$ or $IRES_{CP}$ such that the second gene is placed under the translational control of $IRES_{MP}$ or $IRES_{CP}$. The primary chimeric continuous RNA transcript in positive sense polarity is produced by the transformed cells from the said expressible promoter. The expression of both genes occurs in eukaryotic cells (plant, animal, human and yeast) or in vitro in cell-free protein synthesizing systems; the first gene is expressed by direct translation whereas the translation of the 5'-distal genes of dicistronic or polycistronic mRNA is promoted by $IRES_{MP}$ or $IRES_{CP}$. Tobamovirus genome-derived IRESes are the first IRES sequences functionally active in plant cells described at the time of priority date of this application (May 30, 1997). The IRESes derived from genomes of animal viruses and other IRES-sequences known so far are not active in plant cells.

(A) Autoradiogram of gradient 8–20% polyacrylamide-SDS gels containing [$^{35}$S] methionine-labeled products directed by uncapped the 5'-H-structure carrying transcripts. Concentration of transcripts is 40 (µg/ml).

(B) The mean values for 12 individual translation samples are given. Standard error bars are presented.

Figure 1A:
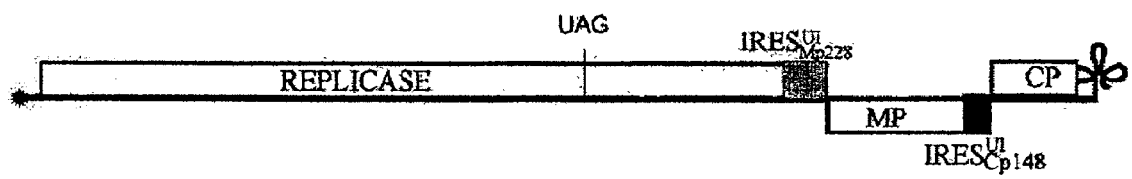
FIG. 1. shows the genetic maps of TMV UI and crTMV (A) The location of $IRES_{MP}$ of crTMV ($IRES_{MP}^{CR}$) and of TMV UI ($IRES_{MP}^{UI}$) as well as that of $IRES_{CP}$ of crTMV ($IRES_{CP}^{CR}$) and TMV UI ($IRES_{CP}^{UI}$) is indicated. Nucleotide sequence and computer predicted secondary structure of $IRES_{MP228}^{CR}$ (B), $IRES_{MP228}^{UI}$ (C), $IRES_{MP75}^{CR}$ (D), $IRES_{MP75}^{UI}$ (E), $IRES_{CP148}^{CR}$ (F), $IRES_{CP148}^{UI}$ (G) and $IRES_{MP228}^{CGMMV}$ (H). Roman numerals in FIG. 1B correspond to the regions I–II of $IRES_{MP,228}^{CR}$ (see also FIG. 4)
Figure 1A:
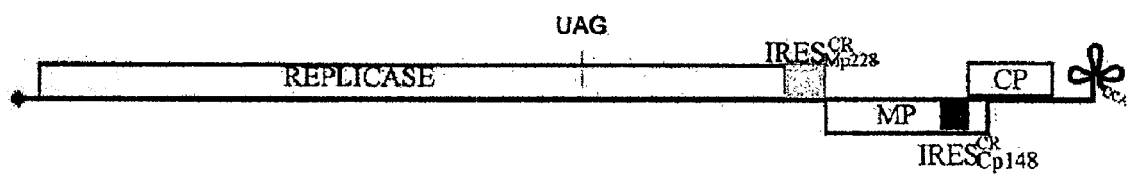
Figure 1B:
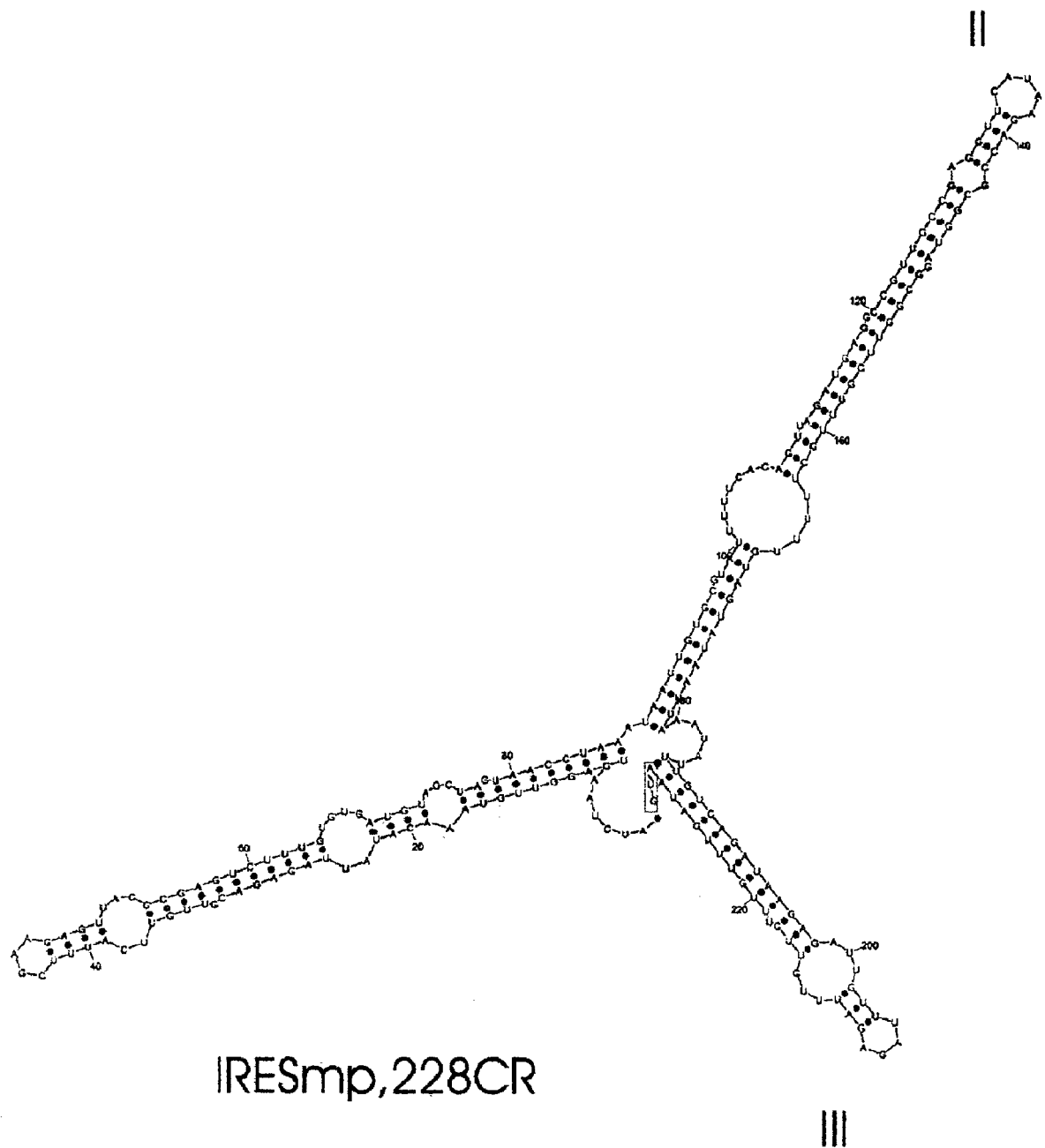
Figure 1C:
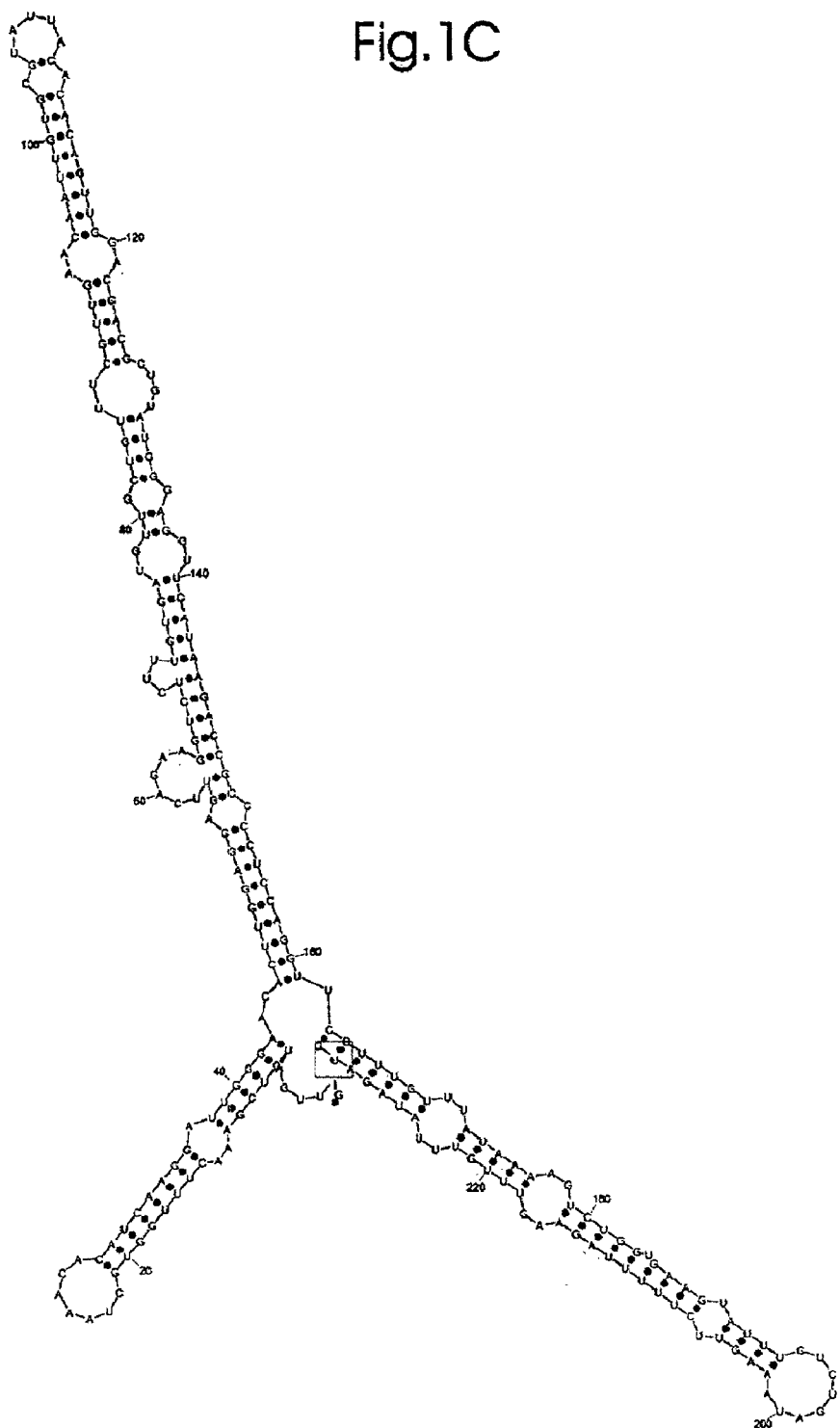
Figure 1D:
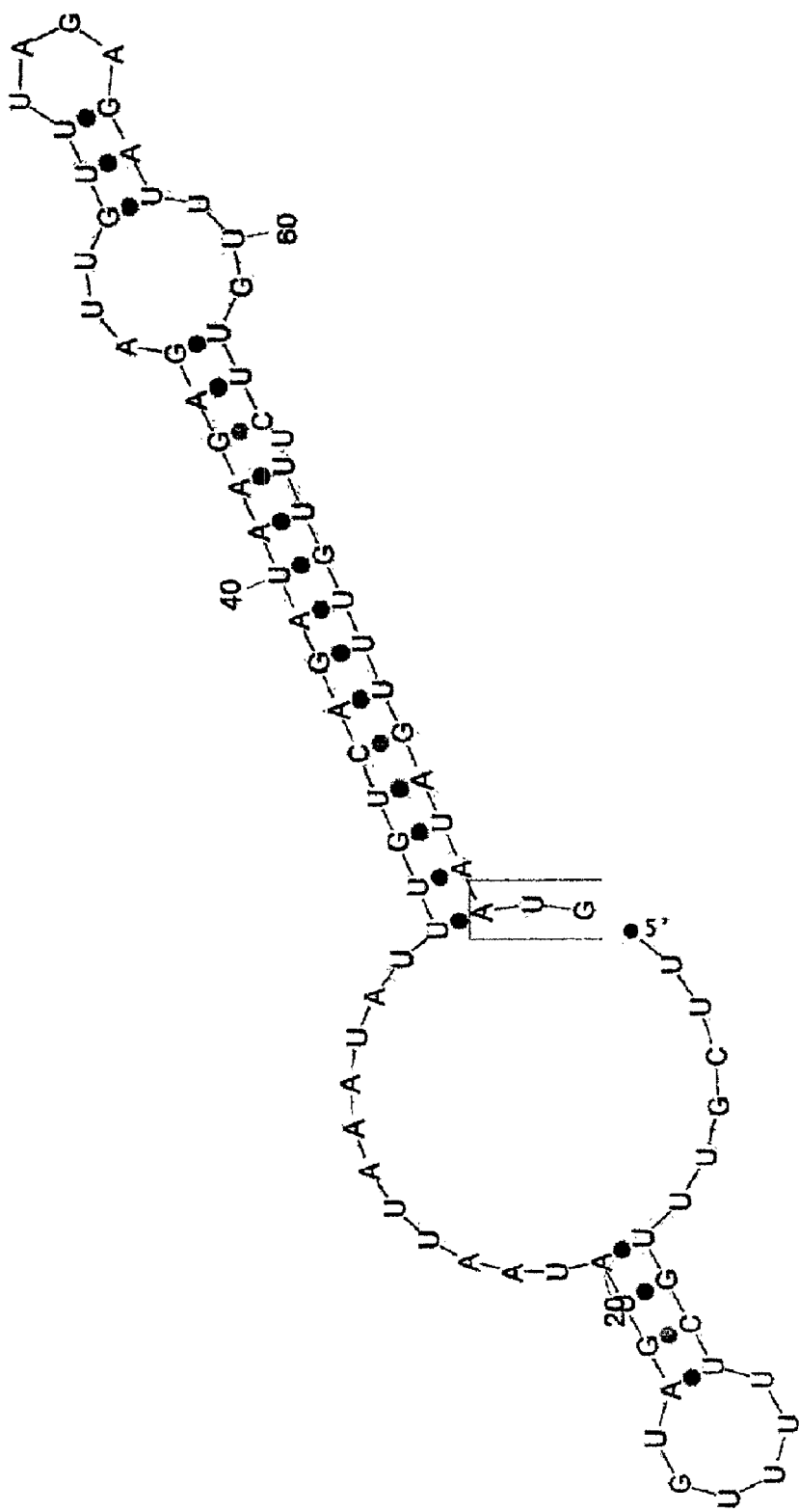
Figure 1E:
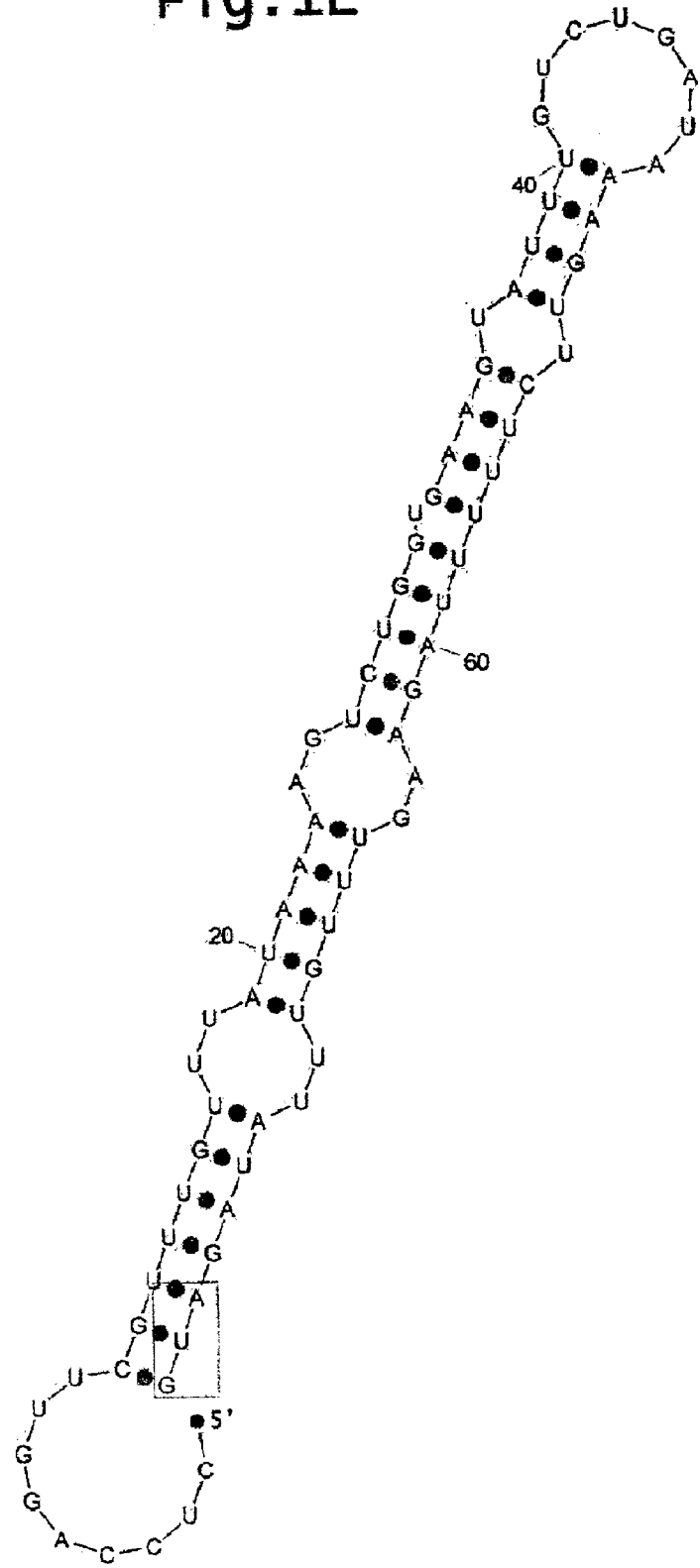
Figure 1F:
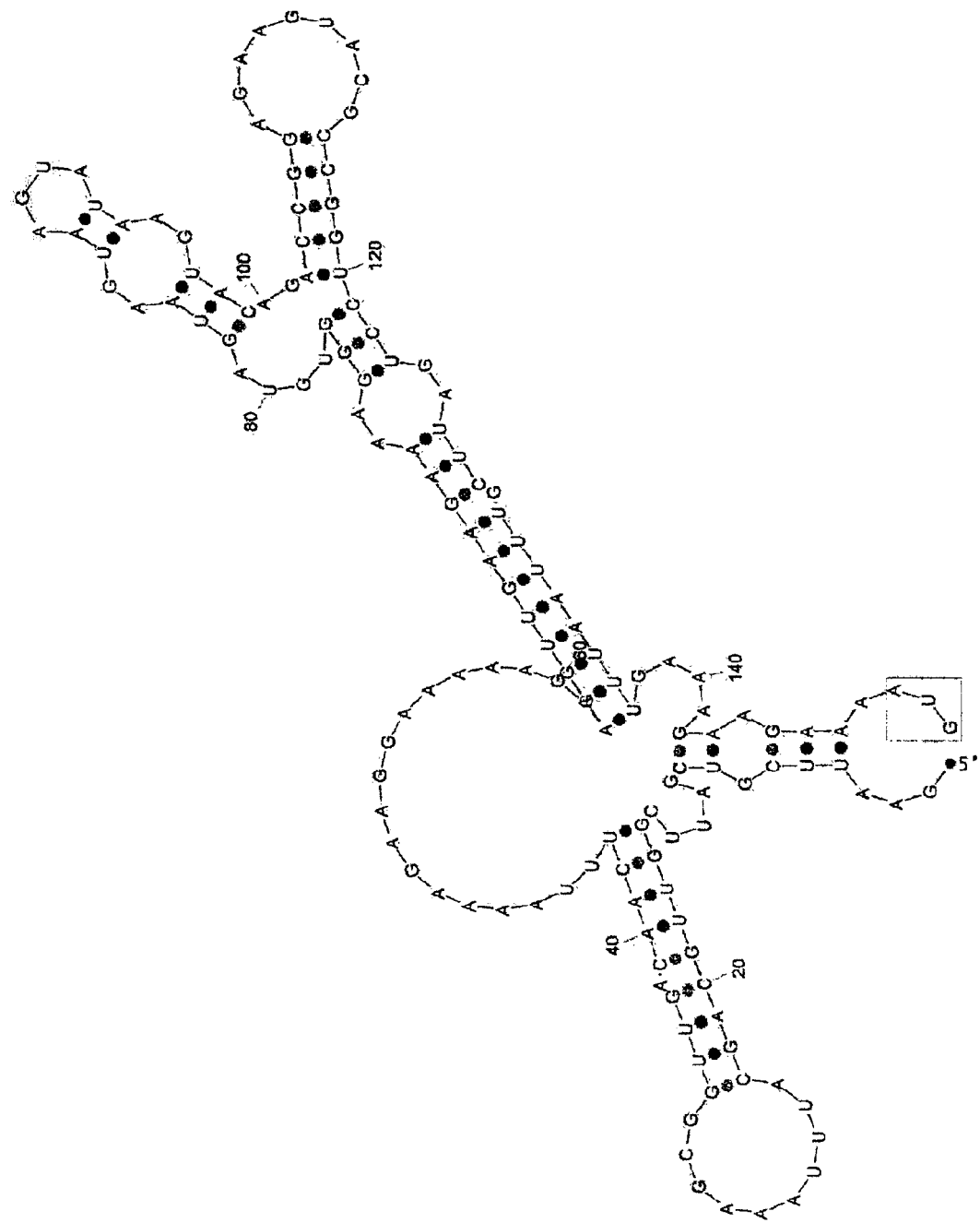
Figure 1G:
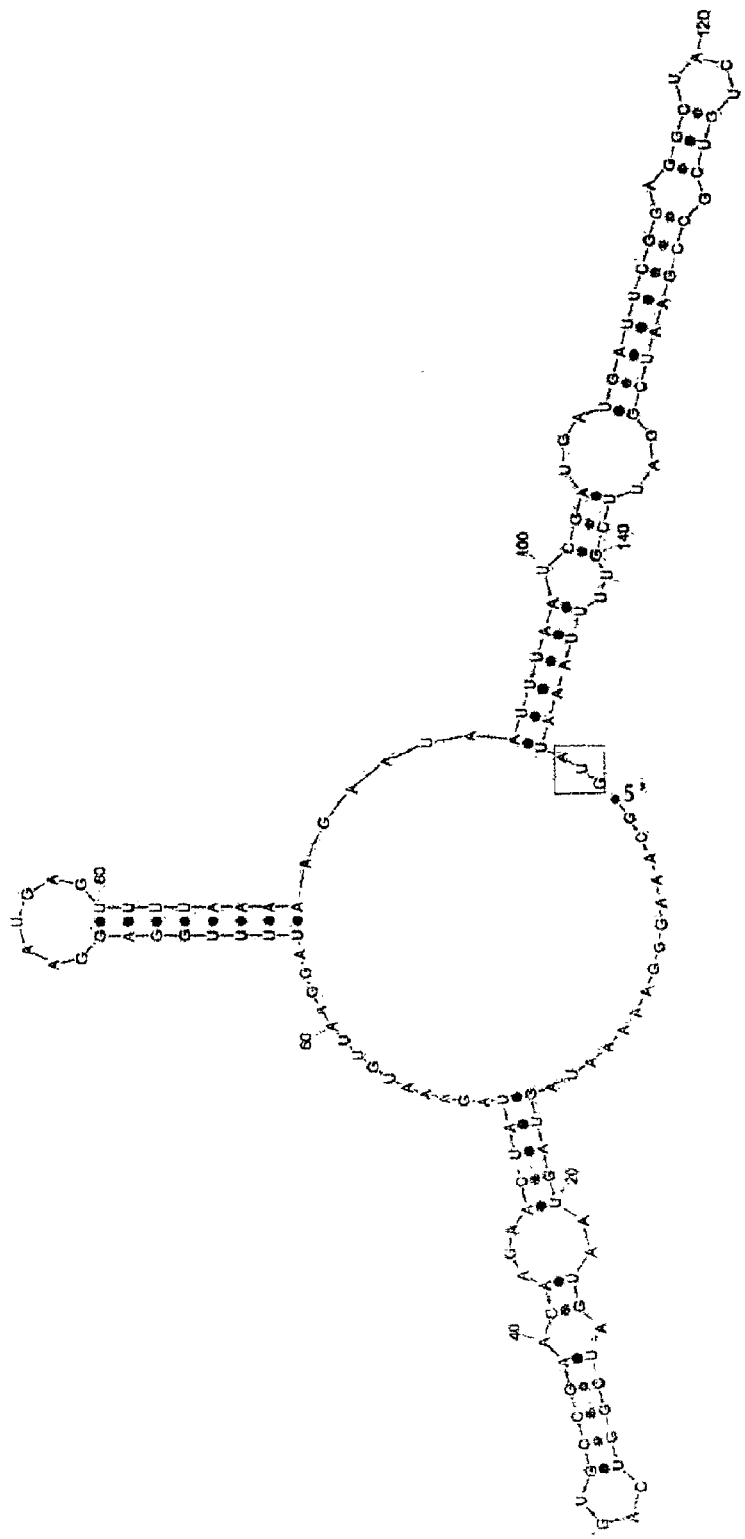
Figure 1H:
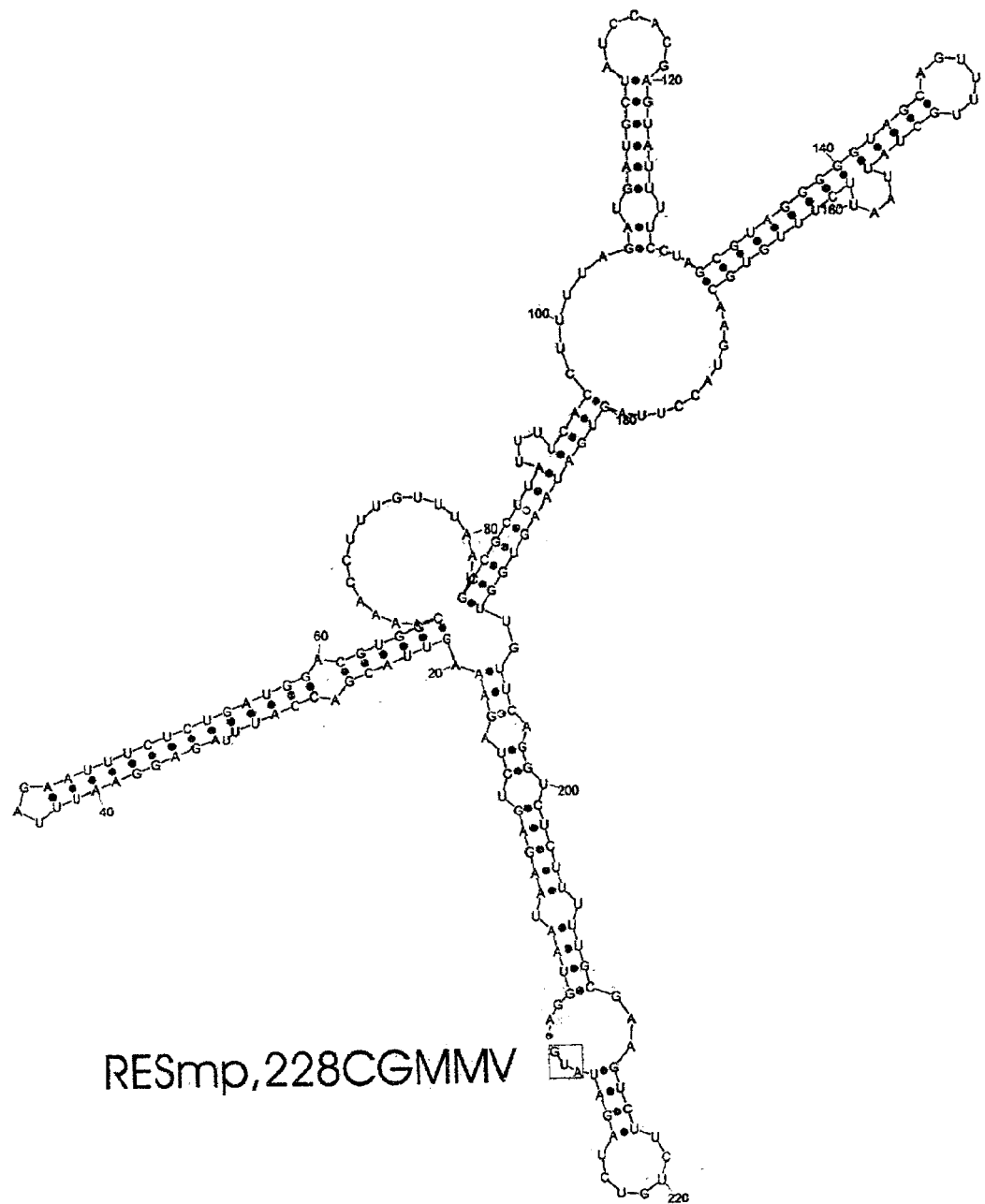
Figure 4:
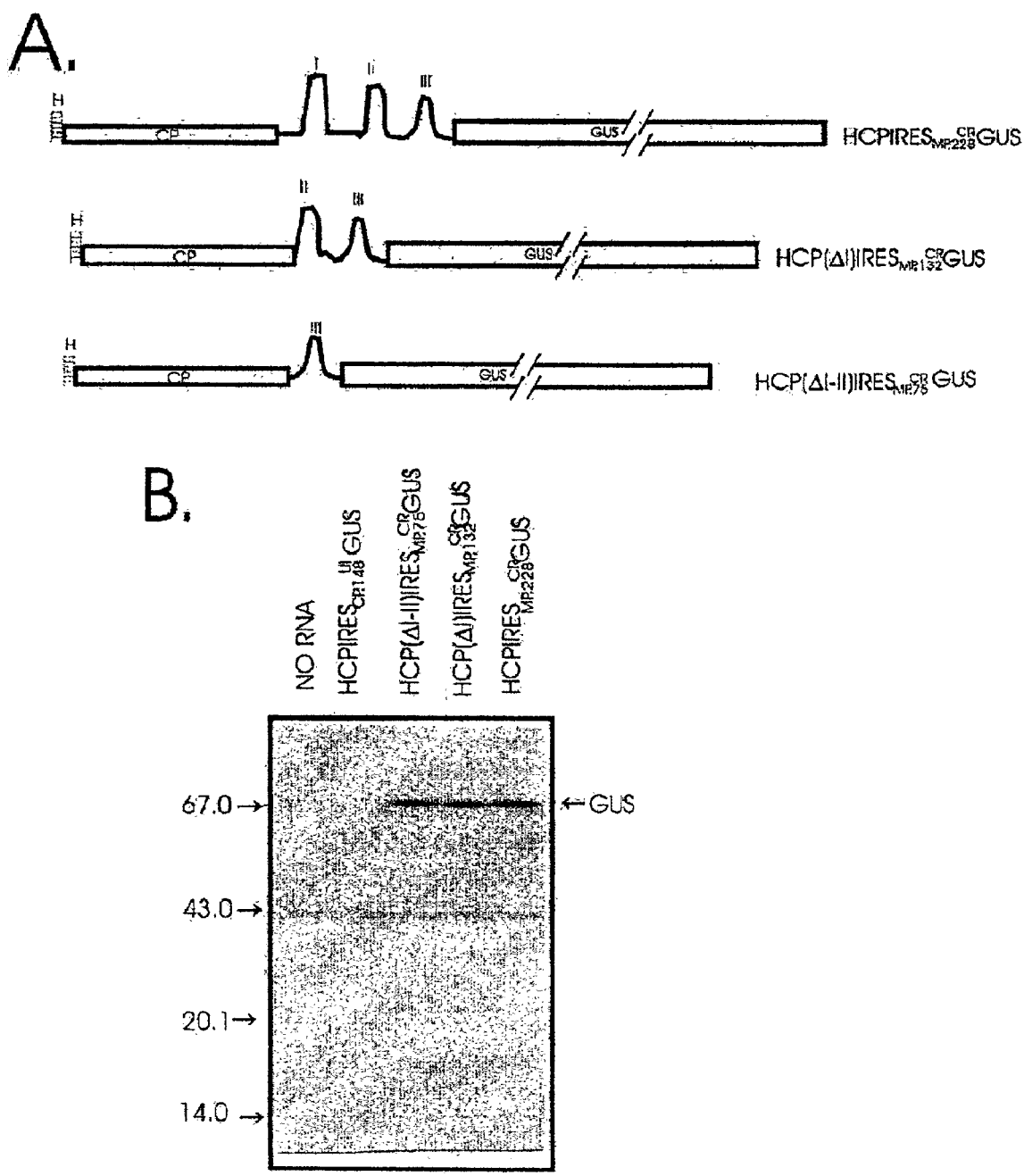

FIG. 4. (A) Schematic representation of the dicistronic chimeric $HCPIRES_{MP,228}^{CR}$GUS transcript and its deletion mutants. Roman numerals denote the regions of $IRES_{MP,228}^{CR}$ depicted in FIG. 1B. (B) Analysis of proteins directed in RRL by dicistronic transcripts HCPGUS containing the 5'-truncated $IRES_{MP}^{CR}$ sequences.

Figure 5:
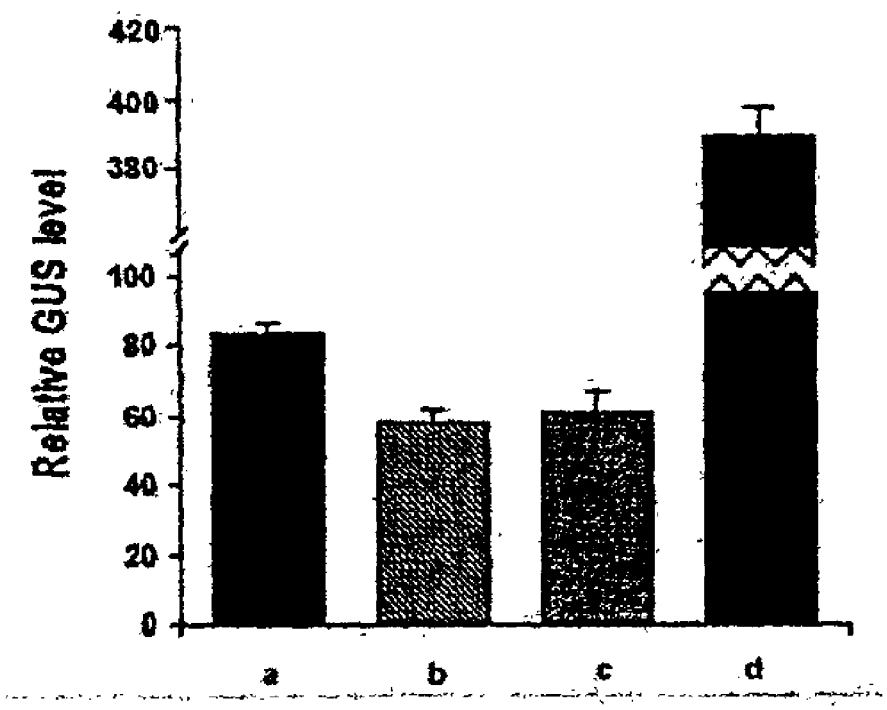

FIG. 5. The dicistronic RNA transcripts HCP-spacer-GUS translated in WGE (Wheat Germ Extracts) contained the following sequences as an intercistronic spacers: $IRES_{MP,228}^{CR}$ (a), $IRES_{CP,148}^{CR}$ (b), $IRES_{MP,75}^{UI}$ (C), and $IRES_{MP,75}^{CR}$ (d).

DETAILED DESCRIPTION OF THE INVENTION

The following definitions are provided to remove ambiguities in the intent or scope of their usage. The term 'expression' refers to the transcription and translation of a gene so that a protein is synthesized. The term 'promoter' refers to a sequence which directs the initiation of DNA transcription. Promoter sequences are necessary to drive the transcription of the downstream gene(s) and include plant-, yeast-or animal-specific eukaryotic promoters. The 35S promoter refers to a plant-expressible cauliflower mosaic virus promoter providing the TATA box and other sequences responsible for maximum efficiency of transcription. This promoter could also serve as a transcriptional recombinant promoter for gene expression in monocotyledonous plants (Last et al., European Patent Application number: 91304205.7) and plant anaerobic regulatory element (Peacock et al., European Patent Application number: 88300852.6). $IRES_{MP}^{CR}$, $IRES_{MP}^{UI}$ $IRES_{MP}^{CGMMV}$ refer to the sequences upstream of MP genes of tobamoviruses (crTMV, TMV UI and cucumber green mottle mosaic virus, CGMMV, respectively). $IRES_{CP}^{CR}$ and $IRES_{CP}^{UI}$ refer to the sequences upstream of the CP genes of crTMV and TMV UI.

A primary objective of this invention is to provide a method which will enable those skilled in the art to express simultaneously two or more desired genes in vitro (in plant-or animal-derived cell-free systems) and in vivo in plant, animal, human and yeast cells transformed by bi-or polycistronic constructs. This objective is to be accomplished by utilising tobamoviral sequences upstream of MP ($IRES_{MP}$) or CP ($IRES_{CP}$) gene (FIG. 1).

Figure 2:
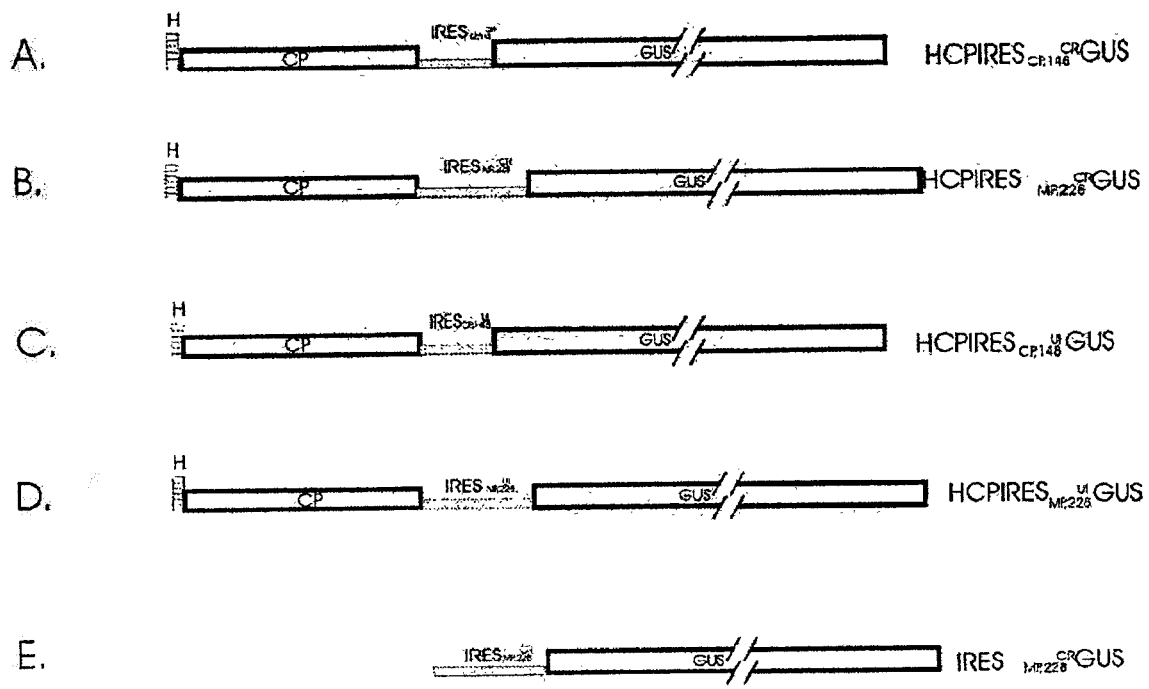
FIG. 2 is a schematic representation of the di- and monocistronic transcripts: (A) $HCPIRES_{CP148}^{CR}$ GUS; the 5'-proximal crTMV CP gene with upstream sequence forming a stable hairpin (H) that abolishes the CP gene translation and GUS gene separated by the 148-nt region upstream of crTMV CP gene ($IRES_{CP148}^{CR}$); (B) $HCPIRES_{MP,228}^{CR}$GUS; the 228-nt region upstream of crTMV MP gene ($IRES_{MP,228}^{CR}$) inserted as the intercistronic spacer; (C) HC $PIRES_{CP,148}^{UI}$GUS; the 148-nt region upstream of TMV UI CP gene ($IRES_{CP,148}^{UI}$) inserted as the intercistronic spacer; (D) $HCPIRES_{MP,228}^{UI}$GUS; the 228-nt region upstream of TMV UI MP gene ($IRES_{MP,228}^{UI}$) inserted as the intercistronic spacer; (E) monocistronic $IRES_{MP,228}^{CR}$GUS.
Figure 3A:
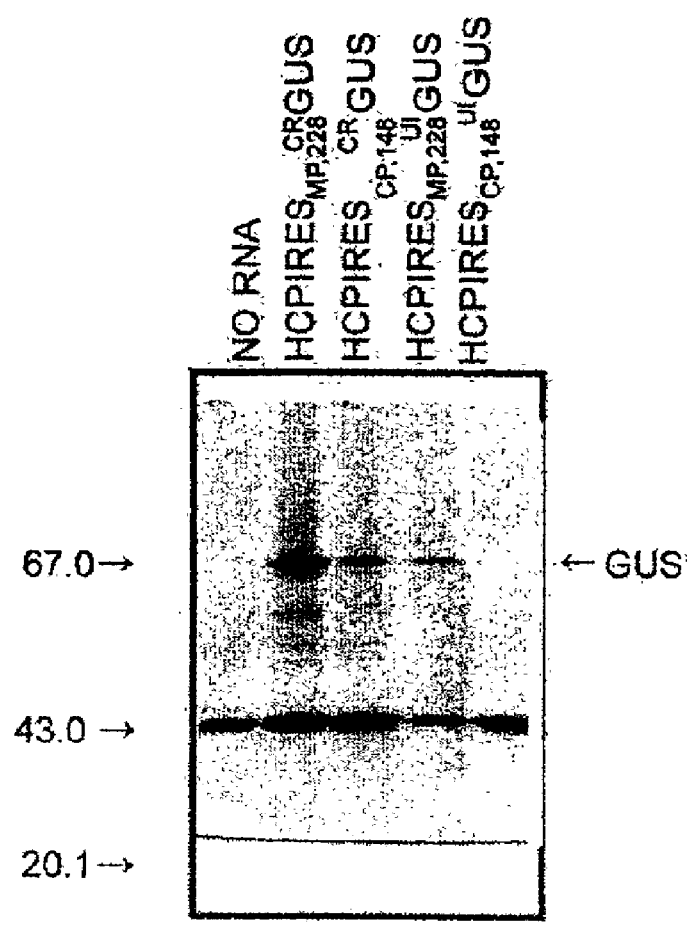
FIG. 3. Analysis of proteins directed in vitro in rabbit reticulocyte lysate (RRL) by the dicistronic chimeric transcripts HCPGUS with different crTMV and TMV UI sequences inserted as the intercistronic spacers (A) and relative efficiencies of $IRES_{MP,228}^{CR}$ and $IRES_{CP,148}^{CR}$ in directing internal initiation of obelin gene from bicistronic 5'-H-structure carrying transcripts (B).
Figure 3B:
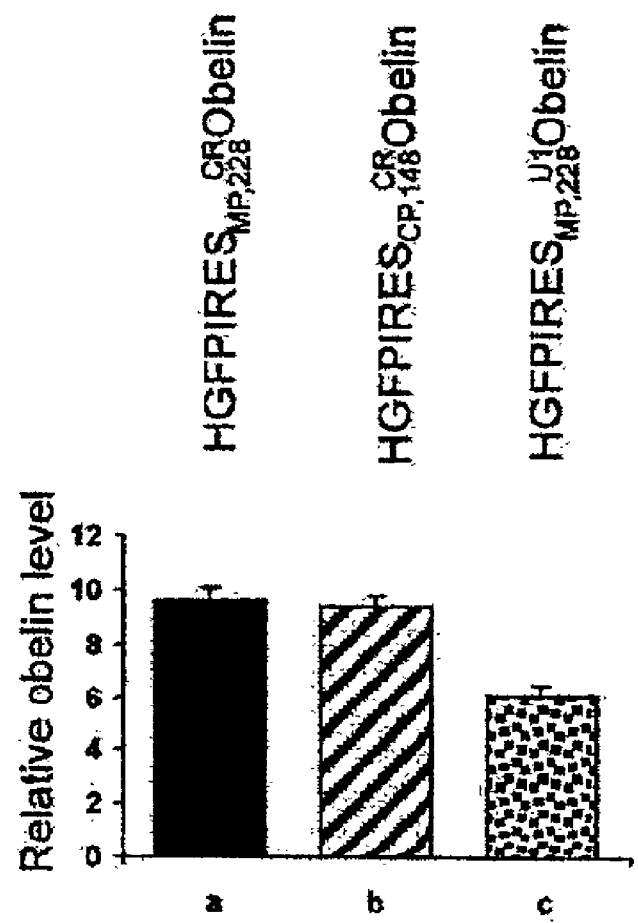

The present invention provides the first proof that the genomic RNAs of tobamoviruses contain regions upstream of the MP and CP genes that are able to promote expression of the 3'-proximal genes from chimeric mRNAs in cap-independent manner in vitro and in vivo. FIGS. 2 and 3 show that the 228-nt sequence upstream from the MP gene of crTMV RNA ($IRES_{MP,228}^{CR}$) mediates translation of the 3'-proximal GUS gene from bicistronic $HCPIRES_{MP,228}^{CR}$GUS transcript. It has been shown that the 75-nt region upstream of the MP gene of crTMV RNA is still as efficient as the 228-nt sequence. Therefore the 75-nt sequence contains an $IRES_{MP}$ element ($IRES_{MP75}^{CR}$) (FIG. 4). It is noteworthy that similarly to crTMV RNA, the 75-nt sequence upstream of the MP gene in genomic RNA of a type member of tobamovirus group (TMV UI) also contains $IRES_{MP75}^{UI}$ element capable of mediating cap-independent translation of the 3'-proximal genes in RRL and WGE (FIG. 5C) Moreover, the 75-nt region upstream from another tobamovirus, cucumber green mottle mosaic virus (CGMMV) was capable of mediating cap-independent expression of the 3'-proximal gene as well (data not presented). It is important that both of $IRES_{MP}^{CR}$ and $IRES_{MP}^{IU}$ were capable of expressing the genes from bicistronic and monocistronic transcripts when the cap-dependent (ribosome scanning) mechanism of translation was abolished by stable hairpin structure (H in FIGS. 3 and 4) which prevented cap-dependent translation.

On the whole, the data presented prove that the sequences upstream of MP and CP genes derived from genomic RNAs of different tobamoviruses contain new IRES elements $IRES_{MP}$ and $IRES_{CP}$, respectively.

The method of this invention involves the construction of recombinant bi-or polycistronic nucleic acid molecule which comprises at least a first expressible reporter gene, $IRES_{MP}$ (or $IRES_{CP}$) and a second expressible reporter gene, the second expressible gene being located 3' to the $IRES_{MP}$ (or $IRES_{CP}$) and positioned such that expression of the second gene is controlled by IRES-sequence derived from a tobamovirus genome. The recombinant nucleic acid molecule may be incorporated into a nucleic acid construct or vector in combination with suitable regulatory sequences (promoter, terminator, enhancer, transit peptide etc). The transit peptide may be homologous or heterologous to the protein of interest and will be chosen to ensure its secretion to the desired organelle or extracellular space. Such a nucleic acid construct may be cloned or transformed into a biological system which allows simultaneous coordinated expression of two or more genes. Suitable biological systems include plants, animals and yeasts, viruses of eukaryotes as well as cultured cells of eukaryotes (such as insect cells, mammalian cells and plant cells).

An important objective of this invention was to show experimentally that tobamoviral $IRES_{MP}$ and $IRES_{CP}$ are functional in vivo, i.e. that they can cap-independently express the 3'-proximal genes in transformed cells. Our results indicate that:

a) $IRES_{MP}^{CR}$-, $IRES_{MP}^{UI}$-, $IRES_{MP}^{CGMMV}$-and $IRES_{CP}^{CR}$-sequences are capable of directing cap-independent translation of the second gene from bicistronic CP-IRES-GUS mRNAs in transient assays (electroporated tobacco protoplasts). It should be emphasized that the efficiency of internal translation (IRES-mediated GUS activity) was as high as 17–21% relative to an inversed bicistronic construct carrying the GUS gene at 5'-position (GUS-IRES-CP) (Table 1);

b) $IRES_{MP}$ and $IRES_{CP}$ sequences are functionally active in vivo in tobacco plants transgenic for bicistronic constructs containing IRES elements as intercistronic spacers. Table 2 shows that IRES-mediated expression of the 3'-proximal GUS gene from bicistronic constructs was as high as 21–31% relative to controls (expression of the GUS gene from monocistronic 35S promoter-based GUS construct or from the 5'-position of bicistronic GUS-IRES-CP construct which is inversed in respect to experimental constructs CP-IRES-GUS).

c) $IRES_{MP}$ and $IRES_{CP}$ sequences were active in vivo in tobacco leaves subjected to microprojectile bombardment: the 3'-proximal GUS gene was expressed from bicistronic constructs in particle bombardment experiments.

d) $IRES_{MP}$ was functionally active not only in plant cells but also in human (HeLa) cells transformed with bicistronic SV40 promoter-based constructs that contained the 5'-gene of green fluorescing protein (GFP) and 3'-proximal GUS gene separated by $IRES_{MP}$ (Table 3). It is important to note that in this construct the cap-dependent translation of the 5'-proximal GFP gene was abolished by a stable hairpin (H) structure. In a negative control the TMV-derived 74-nt 5'-NTR "omega" sequence of TMV RNA was used as intercistronic sequence (Table 2). Therefore, the application of tobamoviral IRES element is not restricted by a plant cell and is efficient in human cells as well;

e) It was found that both tobamoviral $IRES_{MP}$ sequences ($IRES_{MP,75}^{CR}$ and $IRES_{MP,75}^{UI}$) as well as $IRES_{CP,148}^{CR}$ and $IRES_{CP,148}^{UI}$ are functional in yeast cells. The $IRES_{MP,75}^{UI}$ derived from a type TMV UI was even more efficient than $IRES_{MP,75}^{CR}$ in mediating the 3'-proximal GUS gene expression from bicistronic constructs in yeasts (Table 4) Moreover, $IRES_{MP,75}^{UI}$ was considerably more active than the well-known $IRES_{EMCV}$ sequence from RNA of encephalomyocarditis virus. The $IRES_{EMCV}$ is best studied and highly efficient IRES used in biotechnology for cap-independent expression of foreign genes in animal (including human) cells. It is important that the highest activity in expressing the 3'-proximal GUS gene in yeast cells was shown by a plant virus-derived $IRES_{CP}^{CR}$ (Table 4).

It is noteworthy that the 148-nt sequence upstream of the TMV UI CP gene ($IRES_{MP,148}^{UI}$) which is nonfunctional as IRES in vitro and in transformed plant cells (see above) exhibited a moderate IRES activity in yeast cells (Table 4).

The present invention shows that:

(i) The nucleotide sequences located in genomic RNAs upstream of the MP genes of different tobamoviruses ($IRES_{MP}$) promote expression of the 5'-distal genes from bicistronic mRNAs in eukaryotic cells by internal ribo-some entry pathway.

(ii) The nucleotide sequence located upstream of CP gene in genomic RNA of different tobamoviruses ($IRES_{CP}^{CR}$, $IRES_{CP}^{UI}$) promotes expression of the 5'-distal genes from bicistronic mRNAs in eukaryotic cells by internal ribosome entry pathway.

(iii) A unique feature of tobamovirus $IRES_{MP}$ and $IRES_{CP}$ is their ability to exhibit activity not only in transformed plant protoplasts and transgenic plants but also in other types of eukaryotic cells including animal and yeast cells. In addition, majority of tobamovirus IRESes ($IRES_{CP,148}^{UI}$ is the only exclusion) can promote IRES activity in cell-free translation systems of plant (WGE) or animal (RRL) origin.

There are several additional situations when the tobamovirus RNA-derived IRES elements could be used in transient assays and stable transgenic expression constructs to circumvent the constraints of cap-mediated translation and to create polyfunctional RNAs:

a) coexpression of defined gene products in cell culture and transgenic plants and animals. Many in vitro applications for plant and mammalian transgenesis demand the coexpression of heterologous gene products. For example, in order to establish stable cell clones and lines of transgenic plants and animals producing a recombinant protein it is generally necessary to introduce vectors for expression of both the protein of interest and the selectable marker. This is usually achieved either by co-transfecting cells with two independent constructs or by introducing a single vector harboring two discrete expression cassettes. The first approach is often limited by the inefficiency of co-transfection. The second one requires the construction of relatively complex vectors and generally suffers from unreliable and/or low expression of the nonselectable cDNA. The use of an IRES in dicistronic expression vectors can circumvent these problems by enabling a single transcription unit to provide efficient production of both the protein of interest and a selectable marker (Kaufman et al. (1991) Nucleic Acids Res.19: 4485–4490; Ghattas et al. (1991) Mol. Cell. Biol. 11: 5848–5859; Sugimoto et al. (1994) Biotechnology 12: 694–698);

b) Functional expression cloning of novel cDNAs. In addition to facilitating the stable expression of characterized cDNAs, vectors incorporating IRES-mediated coexpression of a selectable marker may also be applied to the isolation of new genes through functional cloning approaches. For instance, one route to the identification of cDNAs that affect the growth or differentiation of a particular cell type is to screen populations of cells transfected with cDNA expression libraries. Vectors with IRES-linked gene expression of a selectable marker promise significant increase in efficiency by ensuring that the majority of selected transfectants also express cDNA. A powerful strategy for cloning cDNAs that encode interacting proteins is the two-hybrid system (Fields and Song (1989) Nature 340: 245–246). This screen is based on the coexpression of a hybrid between a cDNA and an activation domain along with a fusion protein of DNA binding domain and a target protein. The requirement for production of two proteins suggests that the methodology could be simplified by incorporating an IRES element to produce a single vector for coexpression of both fusion proteins. It was shown above (Table 4) that several tobamovirus-derived IRESes are functional in yeast. Certain IRES sequences have recently been demonstrated to work in Saccharomyces cerevisiae (Iisuka et al. (1994) Mol. Cell. Biol. 14: 7322–7330), so this approach could be applicable in yeast as well as in analogous mammalian systems (Vasavada et al. (1991) Proc. Natl. Acad. Sci. USA 88: 10686–10690; Fearon et al. (1992) ibid 89: 7958–7962).

A further objective of this invention is to provide simultaneous expression of plant virus-derived genes (replicase, MP and CP genes) using $IRES_{MP}$ and $IRES_{CP}$, for example, in the following DNA expressing cassettes: replicase gene/$IRES_{MP}$/MP gene/$IRES_{CP}$/CP gene. It is well known that the transgenic plants containing plant virus-derived genes in their genome are resistant to homologous plant viruses due to posttranscriptional gene silencing phenomenon. It is possible lo create transgenic plants resistant to different plant viruses using such a DNA construction. The DNA expressing cassettes may be incorporated into a DNA construction or vector in combination with suitable regulatory sequences (promoter, terminator, transit peptide, enhancer etc). The DNA sequence may be placed under the control of a homologous or heterologous promoter which may be a constitutive or an inducible promoter (stimulated by, for example, environmental conditions, presence of a pathogen, presence of a chemical). Plant cells may be transformed with recombinant DNA constructs according to a variety of known methods (*Agrobacterium* Ti plasmids, electroporation, microinjection, microprojectile bombardment etc). The transformed cells may then in suitable cases be regenerated into whole plants in which the new nuclear material is stably incorporated into the genome. Both transformed monocotyledonous and dicotyledonous plant may be obtained in this way. Examples of genetically modified plants which may be produced include field crops, cereals, fruit and vegetables such as canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

A still further objective of this invention is to express coordinately in transgenic plants a set of genes. Coordinated expression is useful, for example, when it is necessary to express a protein consisting of various polypeptides or when several enzymes of a biosynthetic pathway must be expressed.

A further objective of this invention is to provide the simultaneous production of proteolytic enzymes to cleave a polyprotein product.

The objects of this invention are plants, plant cells and plant tissues grown in fields or specific fermentors. Further objects are vectors and expression cassettes comprising $IRES_{MP}$, and bacterial cells comprising such vectors suitable for maintenance, replication, and plant transformation.

It is to be noted that eukaryotic IRES sequences of plant viral origin may be more widespread than has been realized hitherto, because they cannot be identified by sequence homology; known IRESes have been functionally defined and, so far, no conserved features have been found. Therefore, the present invention is not limited to any specific IRES sequence described here only. Rather this invention describes functional property of any IRES sequence derived from the genome of plant viruses including the tobamovirus group and other plant viruses with plus-sense single stranded RNA genomes.

The invention is further illustrated in the following non-limiting examples and with reference to the figures.

EXAMPLES

Example 1

Construction of IRES-containing plasmids

Standard techniques of molecular biology were carried out according to Maniatis et al. (1982) Molecular Cloning: a Laboratory Manual. Cold Spring Harbor Laboratory, Cold Spring Harbor, N.Y. All plasmids utilized in the invention can be prepared according to the directions of the Specification by a person of ordinary skill in the art without undue experimentation employing materials readily available in the art.

To obtain pCP, crTMV cDNA was amplified by PCR with primers which introduced KpnI site at the 5'-end and HindIII site at the 3'-end of the crTMV CP gene and the product was cloned between the KpnI and HindIII sites of pBluescript II SK+. The plasmid pHCP differs from previous construct by the presence of inverted tandem repeat (KpnI-EcoRI and ClaI-KpnI fragments from pBluescript II SK+polylinker sequence). Cloning of the BamHI/SadI fragment from pTBSMPΔCPSma (described by Ivanov et al. (1997) Virology 232: 32–43) into pCP resulted in formation of pCPMP. This plasmid contains crTMV CP and MP genes with several restriction sites in the intercistronic area. $CPIRES_{MP}MP$ construct was generated by digestion of the pCPMP with EcoRV and BglII followed by insertion of the EcoRV/BglII fragment, derived from pG7S3 crTMV cDNA sequenced clone This clone contained C-terminal part of the replicase gene (EcoRI site) and the 5' terminal coding part of the MP gene (BglII site). To obtain monocistronic construct $IRES_{MP}GUS$, pGEM3zf+ vector was digested with EcoRI and SalI and then ligated with two inserts: GUS-gene (NcoI/SalI fragment from pRTαβGUS described by Zelenina et al. (1992) FEBS Lett. 296: 276–270) and EcoRI/NcoI-cut PCR-product which was amplified from crTMV cDNA clone pG7S20 (Ivanov et al. (1997) Virology 232: 32–43) using primers which introduced EcoRI and KpnI sites at the 5'-end and NcoI site at the 3'-end of the $IRES_{MP}$ sequence (228 nucleotides upstream of the crTMV MP gene). The EcoRI/PstI fragment of IRESmpGUS was inserted into EcoRI/PstI-cut pHCP to give dicistronic construct pHCPIRESmpGUS. The plasmid UIspGUS was created by cloning two fragments (HindIII/NcoI-cut UIspGUS and NcoI-XbaI-cut GUS gene) between the HindIII and XbaI sites of Bluescript II SK+. UIsp was obtained in RT-PCR using genomic TMV UI RNA with 5'-oligonucleotide primer corresponding to 4676–4686 of the TMV UI cDNA containing HindIII site and the 3'-primer containing NcoI site and complementary to nucleotides 4883–4903 of the TMV UI cDNA. GUS gene was obtained by digesting pRTαβGUS plasmid with NcoI and XbaI. The HindIII/XbaI fragment of UIspGUS was cloned into HindIII/XbaI-cut pHCP to obtain pHCPUIspGUS. The creation of αβGUS was described by Ivanov et al. (1997) (Virology 232: 32–43).

The pFF series of constructs have 35S-enhancer, 35S-promoter and 35S-polyadenylation signal (Topfer et al. (1987) Nucleic Acids Res. 415: 5890). These plasmids were derived from pFF19 and pFF19GUS constructs described earlier (Morozov et al. (1997) J. Gen. Virol. 78: 2077–2083). The constructs pFFCPIREScpGUS, pFFCPIRESmpGUS and pFFCPUIspmpGUS were generated by cloning KpnI/XbaI-fragments of CPIRESmpGUS and CPUIspmpGUS, respectively, into pFF19 vector.

Example 2

In vitro transcription

The plasmids HCPIRESmpGUS, HCPIREScpGUS, HCPUIspGUS, αβGUS, UIspGUS were linearized by SacI. The recombinant plasmids were transcribed in vitro as described by (Tomashevskaya et al. (1993) J. Gen. Virol. 74: 2717–2724). Agarose gel electrophoresis of RNA transcripts confirmed that they were intact. The RNA concentration was quantified by agarose gel electrophoresis and spectrophotometry.

Example 3

IRES-mediated expression of the 3'-proximal genes in cell-free systems

In vitro translation in rabbit reticulocyte lysates (RRL) was performed as described by Pelham and Jackson (1976) (Eur. J. Biochem 67: 247–256) with minor modifications. Translation mixture (25 μl final volume) contained 10 pl nuclease-treated lysate containing 1 mM $CaCl_2$ with hemin; 20 mM Hepes, pH 7.6; 1 mM ATP; 200 mM GTP; 2.5 mM magnesium acetate; 100 mM potassium acetate; 2 mM DTT; 15 mM creatine phosphate; 1 μg creatine phosphokinase; 5 mM cAMP; 2 mM EGTA; 3 μg yeast tRNA; 125 μM of each essential amino acid excluding methionine; 800 μCi/ml [$^{35}$S]-methionine (Amersham, >1000 Ci/mmol) and 40–100 μg/ml of virus RNA. Incubation was carried out at 30° C. for 60 min. Translation in wheat germ extracts (WG) was performed according to the manufacturer's (Promega) protocol in the presence of [$^{35}$S]-methionine for 60 min at 25° C. Radiolabeled translation products were analysed by SDS-PAGE and localized by autoradiography on the dried gel.

It has been known for a long time that only the 5'-proximal gene of tobamovirus genomic RNA can be directly translated by ribosomes. A dicistronic uncapped sgRNA called $I_2$ directs translation of only MP, while a second, capped monocistronic sgRNA directs synthesis of the CP (reviewed by Palukaitis and Zaitlin (1986) in The Plant Viruses, eds. Van Regenmortel and M.Fraeukel-Conrat, 2: 105–131, Plenum Press).

The question arises as to whether the sequences upstream of the MP gene of tobamoviruses contain IRES elements capable of mediating cap-independent translation of the 3'-proximal gene from bicistronic transcripts. Therefore, chimeric bicistronic constructs containing the 3'-proximal GUS gene and different 5'-proximal genes were constructed. The two genes of bicistronic constructs were separated by different intercistronic sequences used in this and subsequent Examples: a) the sequence (75–228 nt long) upstream of the crTMV MP gene ($IRES_{MP,228}^{CR}$, $IRES_{MP,132}^{CR}$ $IRES_{MP,75}^{CR}$); b) the 75-nt sequence upstream of the MP gene of type TMV UI ($IRES_{MP75}^{UI}$); c) the 148-nt sequence upstream of the CP gene of crTMV ($IRES_{CP,148}^{CR}$); d) the equivalent sequence from RNA of TMV UI ($IRES_{CP,148}^{UI}$) in vitro and in plant cells. However, this sequence was functionally active in transformed yeast cells ($IRES_{CP,148}^{UI}$ in Table 4).

The chimeric IRES-carrying mRNA transcripts in particular cases contained a stable 5' hairpin structure (H) which was shown to abolish the translation of the 5'-proximal gene. Consequently, the translation of the 3'-proximal gene from these H-carrying transcripts indicated that intercistronic IRES sequences were functionally active in promoting cap-independent translation (FIGS. 2, 3 and 4).

In order to demonstrate that $IRES_{MP}$ -mediated translation is not unusual for tobamoviruses, the equivalent dicistronic construct ($HCPIRES_{MP,228}^{UI}GUS$) was made containing the 228-nt region upstream of TMV UI MP gene as an intercistronic spacer (FIG. 3). FIGS. 4 and 5 show that crTMV-derived and TMV UI-derived $IRES_{MP}$ sequences were capable of mediating internal ribosome entry even being truncated to 75- nt $IRES_{MP,75}^{CR}$ and $IRES_{MP,75}^{UI}$, respectively. It is worth mentioning that $IRES_{CP}$-and $IRES_{MP}$-containing dicistronic RNA-transcripts that retained their integrity during incubation in translation extract (Skulachev et al. (1999) Virology 263: 139–154). In a separate experiment (not presented) we found that the 75-nt sequence upstream from the MP gene of one more tobamovirus, cucumber green mottle mosaic virus, exhibited the $IRES_{MP,75}^{CGMMV}$ activity promoting the cap-independent expression of 3'-proximal GUS gene.

Example 4

IRES-mediated transient expression of the 3'-proximal GUS gene in tobacco protoplasts The following procedures of protoplast preparation and transfection were used: (i) The protoplasts were isolated from N. tabacum (cv. W38) leaves as described (Saalbach et al. (1996) Plant Physiol. 112: 975–985). Aliquots of 4×10$^5$ protoplasts were co-electroporated (electric impulse of 1 ms at 750 V/cm) with 10 μg of pFF19-based dicistronic DNA constructs "CP-spacer-GUS" and 10 μg of pCLN DNA containing the firefly luciferase (LUC) gene (Callis et al. (1987) Genes Dev. 1: 1183–1200) and incubated for 18 hours at 25° C. in the dark. GUS activity was measured as relative light units (RLU) by TROPIX GUS-light kit following the manufacturer's protocol and using LKB 1251 Wallac luminometer. GUS activity was determined according to (Jefferson (1987) Plant Mol. Biol. Rep. 5: 387–405). For each experiment background GUS activity associated with non-transfected protoplasts was subtracted throughout. Protein concentration was estimated using a Bio-Rad protein assay kit based on the method of Bradford (1976) (Anal. Biochem. 72: 248–254).

Table 1 shows relative GUS expression in tobacco protoplasts transformed with IRES-containing bicistronic constructs. It can be seen that the level of the 3'-proximal GUS gene expression mediated by $IRES_{MP}^{CR}$ and $IRES_{CP}^{CR}$ was high enough.

Example 5

Particle bombardment

Particle bombardment was performed using flying disk method (e.g, see Daniell (1993), Methods in Enzymology 217: 537–557) with high-pressure helium-based apparatus PDS-1000 (Bio-Rad). Briefly, for each series of shots, DNA was precipitated on tungsten particles with calcium chloride and ethanol after the addition, while vortexing, of 10 μl of plasmid DNA (at 0.5–1.5 mg/ml to 6 mg of tungsten particles suspended in 100 μl of 50% glycerol, and then the tungsten particles were kept in suspension in cold 95% ethanol (90 mg/ml). After sonication 5 μl of this mixture was placed immediately on each plastic flying disk and used for bombardment when the particles had dried. A detached leaf of Nicotiana benthamiana (15–30 mm size) was placed in the center of a plastic Petri dish and bombarded on a solid support at a target distance of 7 cm. Bombardment was done with a pulse of 1350 kPa helium gas in a vacuum chamber.

Inoculated leaves were sampled 24 to 72 hrs after bombardment. IRES activity was monitored by histochemical detection of GUS expression as described by Jefferson (1987) (Plant Molecular Biology Report 5: 387–405). Samples were infiltrated in the calorimetric GUS substrate, modified (De Block and Debrouwer (1992) Plant J. 2: 261–266) to limit the diffusion of the intermediate products of the reaction: 0.115 M phosphate buffer, pH 7.0, containing 5-bromo-4-chloro-3-indolyl-β-D-glucuronide (X-Gluc) 600 µg/ml; 3 mM potassium ferricyanide; 10 mM EDTA. After incubation overnight at 37° C., the leaves were fixed in 70% ethanol and examined by light microscopy.

It was found that 35S-based DNA constructs CPIRES$_{CP}$-GUS and CPIRES$_{MP}$GUS were active in GUS synthesis in bombarded leaves as was shown by histochemical reactions (data not presented).

Example 6

IRES-mediated expression of the 3'-proximal GUS gene in transgenic tobacco

Transgenic tobacco was constructed as described by Malyshenko et al. (1993) (J. Gen. Virol. 74: 1149–1156). GUS testing was performed as described in Example 4. Integrity of DNA constructs insertion in plant genome was confirmed by PCR analysis. The results of GUS testing in R$_0$ transgenic plants are presented in Table 2. It can be seen that the efficiency of the 3'-proximal GUS gene expression from bicistronic constructs mediated by IRES$_{MP}$ and IRES$_{CP}$ was as high as 20–31% relative to the GUS gene expression from 5'-position in controls.

Example 7

IRES-mediated expression of the 3'-proximal GUS gene in human cells

3–5×10$^4$ HeLa cells were transformed with 0.25 µg of SV40-based vector pcDNA3.1 (Invitrogen) (as a mock-transformation) or with this vector containing bicistronic DNA where IRES$_{MP,75}^{CR}$ or TMV omega sequence were used as intercistronic spacers. After 44 hours of incubation the cells were lysed with 250 µl of Tris/SDS buffer by freezing and 100 µl from each sample were analysed for GUS activity after 60 min of incubation (Bradford (1976) Anal. Biochem 72: 248–254).

Table 3 shows that the IRES sequences derived from the genome of a tobamovirus are functionally active in human (HeLa) cells in vivo. This is in line with the results of in vitro translation showing that tobamovirus IRES sequences were functionally active in both WGE and in animal cells-derived cell-free system (FIGS. 3A, 4B).

Example 8

IRES-mediated expression of the 3'-proximal GUS gene in yeast cells

Yeast transformation and induction of gene expression. The yeast strain 2805 was transformed Hill et al. (1991). Nucl. Acid. Res 19: 5791 by pYe-CP-IRES$_{CP}$-GUS and pYe-CP-UI$_{CP}^{SP}$-GUS plasmids. Three ml of yeast night cultures were grown in YPD (1% yeast extract, 2% peptone, 2% dextrose) to an OD$_{600}$ of 0.2. The cultures so obtained were grown for 3 hours at 30° C. After harvesting by centrifugation and washing with sterile water the cells were resuspended in 0.5 ml of LiAc/TE solution (1 M lithium acetate, 1 M Tris-HClpH 7.5, 0.5 M EDT,). 2 µg of melted plasmid DNA (10 minutes at 100° C., rapid chilling in ice) were added to 0.1 ml of yeast cells, mixed and incubated for 10 minutes in the ice bath. 0.6 ml of PEG/LiAc solution (1 M lithium acetate, 1M Tris-HCl pH 7.5, 0.5M EDTA, 50% PEG$_{4000}$) was added with mixing. The yeast cells were grown for 30 minutes at 30° C. After adding DMSO and vortexing, the cells were incubated for 10 minutes at 42° C., then rapidly chilled in ice. The yeast cells were harvested by centrifugation, washed in sterile water, resuspended in 0.3 ml of water and the aliquots of 0.1 ml were incubated for 3 days at 30° C. on Petri dishes with agar medium without histidin. Induction of gene expression from inserted plasmid constructs was performed by growing of transformed yeast clones for 48 hours at 30° C. in the 3 ml of galactose-enriched medium.

Extraction of total protein from yeasts. The yeast cells were harvested by centrifugation. The spheroplasts were obtained by resuspending the cell pellet in the lysis solution I (1 M sorbitol, 0.5M EDTA, liticase (10 µ/µl )) with further incubation for 40 minutes at 37° C. Yeast spheroplasts were harvested by centrifugation and resuspended in 100 µl of lysis solution II (50 mM sodium phosphate pH 7.0, 10 mM EDTA, 0.1% sarkosyl, 0.1% Triton X-100), freezed in liquid nitrogen and rapidly warmed up to 42° C. Freeze/thaw procedure was performed three times. After centrifugation (14000 Rpm, 5 min) the supernatant was taken and the total protein quantity was detected (Bradford (1976) Anal. Biochem 72: 248–254).

Extraction of total RNA from yeasts. RNA was isolated according to Schlnitt et al. Nucl. Acid. Res. 18: 3091–3092 (1990). Table 4 shows that: (i) the IRES sequences derived from the genome of tobamoviruses (crTMV and TMV UI) as well as IRES$_{EMCV}$ derived from animal virus (EMCV) are capable of promoting the 3'-proximal GUS gene expression from bicistronic constructs in transformed yeast cells; (ii) the 148-nt sequence upstream of the CP gene of TMV UI, which is nonfunctional as IRES in plant cells in vivo and in WGE, in vitro (see above), exhibited a moderate IRES activity in yeast cells; (iii) the efficiency of different IRES elements derived from genome of tobamoviruses varied in yeast cells: IRES$_{CP,148}^{CR}$ and IRES$_{MP,75}^{UI}$ were most efficient. Our results show that the efficiency of a tobamovirus-derived IRESes varies dramatically in different types of cells transformed with the same bicistronic constructs. Thus: the efficiency of (i) IRES$_{MP,228}^{UI}$ was negligible in tobacco protoplasts (see FIG. 6 in Skulachev et al. (1999) Virology 263: 139–154) the IRES$_{MP,75}^{UI}$ derived from the region upstream of the MP gene of TMV UI was about 6-fold less active than IRES$_{MP,75}^{CR}$ in cell-free translational system (FIG. 5 in Example 3), whereas in transformed yeast cells IRES$_{MP,75}^{UI}$ was 6-fold more active than IRES$_{MP,75}^{CR}$ (Table 4). Therefore, the efficiency of sequences located upstream of the MP and CP genes in tobamovirus genome is unpredictable in different types of cells. An extreme example is presented by sequence upstream of the CP gene of TMV UI which has no IRES activity in plant cells (see above) but exhibited a moderate IRES activity in yeast cells (Table 4). By contrast, $IRES_{MP,75}^{CR}$ is highly active in transgenic tobacco (Table 2) and HeLa cells (Table 3) but is only moderately active in yeast cells (Table 4).

TABLE 1

TRANSIENT EXPRESSION OF THE 3'-PROXIMAL GUS GENE FROM BICISTRONIC IRES-CARRYING CONSTRUCTS IN TOBACCO PROTOPLASTS TRANSFORMED WITH BICISTRONIC cDNA

| Construct used | Relative GUS expression (%) |
|---|---|
| $CP-IRES_{CP148}^{CR}-GUS$ | 21.3 |
| $CP-IRES_{MP228}^{CR}-GUS$ | 17.7 |
| $GUS-IRES_{CP148}^{CR}-CP$ (control) | 100.0 |

(a) Relative GUS level is expressed in % to bicistronic control construct $IRES_{CP148}^{UI}$ containing the GUS gene of the 5'-proximal position, where the GUS gene can be directly translated by the ribosome-scanning pathway from structurally bicistronic transcript. Mean results of 3 independent experiments are presented.
(b) The 148-nt sequence upstream from the CP gene of TMV UI used as an intercistronic spacer was nonfunctional in tobacco protoplasts and taken as a background GUS level (0.5%) and subtracted throughout.

TABLE 2

EXPRESSION OF THE 3'-PROXIMAL GUS GENE FROM BICISTRONIC IRES-CARRYING CONSTRUCTS IN TRANSGENIC TOBACCO PLANTS TRANSFORMED WITH BICISTRONIC PLASMIDS

| Constructs used | Lines of transgenic plants | Relative GUS expression in RLU/ protein* | Average (±SE) | Relative GUS expression (%) |
|---|---|---|---|---|
| $CP-IRES_{CP,148}^{CR}-GUS$ | 3-11 | 255.56 | 243.78 ± 26 | 31.28 |
|  | 3-5 | 218.46 |  |  |
|  | 3-9 | 237.14 |  |  |
|  | 3-3 | 93.68 |  |  |
|  | 3-3-1 | 340.00 |  |  |
|  | 3-3-2 | 297.65 |  |  |
|  | 3-12 | 170.00 |  |  |
|  | 3-20 | 80.00 |  |  |
|  | 3-4 | 90.67 |  |  |
|  | 3-15 | 183.64 |  |  |
|  | 3-8 | 252.94 |  |  |
| $CP-IRES_{MP,75}^{CR}-GUS$ | 12-5 | 80.00 | 161.79 ± 18 | 20.75 |
|  | 12-5-3 | 120.00 |  |  |
|  | 12-17 | 283.16 |  |  |
|  | 1-18 | 91.11 |  |  |
|  | 1-19 | 248.00 |  |  |
|  | 1-9 | 212.94 |  |  |
|  | 1-9-1 | 168.24 |  |  |
|  | 12-3 | 137.89 |  |  |
|  | 1-3 | 132.50 |  |  |
|  | 12-5-1 | 176.84 |  |  |
|  | 12-2-1 | 132.86 |  |  |
|  | 12-2-2 | 157.89 |  |  |
| $CP-IRES_{MP,228}^{CR}-GUS$ | 2-8 | 286.00 | 163.84 ± 27 | 21.02 |
|  | 2-3 | 216.00 |  |  |
|  | 2-44 | 127.69 |  |  |

TABLE 2-continued

EXPRESSION OF THE 3'-PROXIMAL GUS GENE FROM BICISTRONIC IRES-CARRYING CONSTRUCTS IN TRANSGENIC TOBACCO PLANTS TRANSFORMED WITH BICISTRONIC PLASMIDS

| Constructs used | Lines of transgenic plants | Relative GUS expression in RLU/ protein* | Average (±SE) | Relative GUS expression (%) |
|---|---|---|---|---|
|  | 2-28 | 237.50 |  |  |
|  | 2-29 | 100.00 |  |  |
|  | 2-35 | 120.00 |  |  |
|  | 2-1 | 98.82 |  |  |
|  | 2-24 | 124.71 |  |  |
| $GUS-IRES_{CP,148}^{CR}-CP$ (control I) | 7-19 | 630.59 | 735.36 ± 97 | 94.39 |
|  | 7-19-1 | 560.00 |  |  |
|  | 7-12 | 842.50 |  |  |
|  | 7-12-1 | 1101.80 |  |  |
|  | 7-11 | 657.33 |  |  |
|  | 7-6 | 837.33 |  |  |
|  | 7-2 | 290.00 |  |  |
|  | 7-5 | 963.33 |  |  |
| GUS (control II) | 6-2 | 691.60 | 779.43 ± 52 | 100.00 |
|  | 6-2-1 | 920.00 |  |  |
|  | 6-1-1 | 728.89 |  |  |
|  | 6-1-2 | 860.00 |  |  |
|  | 6-3-1 | 696.67 |  |  |

*RLU-relative light units

TABLE 3

EXPRESSION OF THE 3'-PROXIMAL GUS GENE FROM BICISTRONIC IRES-CARRYING TRANSCRIPTS IN HeLa CELLS TRANSFORMED WITH BICISTRONIC PLASMIDS

| Constructs used | Relative GUS expression (RLU/protein) |
|---|---|
| $H-GFP-IRES_{MP75}^{CR}-GUS$ | 11,249 ± 2184 |
| H-GFP-Omega-GUS | 2,197 ± 313 |
| Mock (pcDNA3.1)[a] | 1,042 ± 36 |

[a]The plasmid pcDNA3.1 was electroporated.

TABLE 4

GUS ACTIVITY IN YEAST CELLS TRANSFORMED WITH BICISTRONIC PLASMIDS*

| Construct used | Relative GUS expression in RLU/protein |
|---|---|
| $CP-IRES_{CP148}^{CR}-GUS$ | 1724 ± 60 |
| $CP-IRES_{MP75}^{UI}-GUS$ | 756 ± 5 |
| $CP-IRES_{MP75}^{CR}-GUS$ | 128 ± 7 |
| $CP-IRES_{EMCV}-GUS$ | 200 ± 7 |
| $CP-IRES_{CP148}^{UI}-GUS$ | 83 ± 1 |
| PYe vector (negative control) | 2.0 |

*The mean values for 5 independent experiments are given.

What is claimed is:

1. An isolated nucleic acid molecule containing an internal ribosome entry site (IRES) of a movement protein gene of a tobamovirus.

2. The isolated nucleic acid molecule according to claim 1, which is derived from a crucifer tobamovirus.

3. A recombinant DNA molecule comprising:

(a) a transcriptional promoter;

(b) a first plant-expressible gene linked to said transcriptional promoter;

(c) a cDNA sequence element designated as an internal ribosome entry site (IRES), which is located 3'to the first plant-expressible gene and wherein said IRES is a eukaryotic, plant-specific IRES that originates from a tobamovirus; and (d) a second plant-expressible gene, located 3'to said IRES such that the second plant expressible gene is under translational control of the IRES;

wherein said first plant-expressible gene or said second plant-expressible gene is a selectable marker.

4. A eukaryotic cell transformed with a recombinant DNA molecule according to claim 3.

5. A transgenic plant containing the recombinant DNA molecule according to claim 3.

6. The recombinant DNA molecule according to claim 3, which additionally comprises in 3' position of said second plant expressible gene a different or the same IRES, and a gene encoding a desired polypeptide.

7. A process for producing stable cell clones or lines, or transgenic plants, which produce a protein of interest, which comprises introducing into cells a recombinant DNA molecule comprising (a) a transcriptional promoter;

(b) first plant-expressible gene linked to said transcriptional promoter;

(c) a cDNA sequence designated an internal ribosome entry site (IRES), which is located 3' to the first plant-expressible gene, whereby said IRES is a eukaryotic, plant-specific IRES that originates from a tobamovirus;

(d) a second plant-expressible gene located 3' to said IRES such that the second gene is placed under the translational control of said IRES, wherein said first plant-expressible gene or said second plant-expressible gene is selectable marker.

8. The process according to claim 7, wherein said IRES is a tobamovirus movement protein IRES ($IRES_{MP}$).

9. The process according to claim 7, wherein said IRES is a tobamovirus coat protein IRES ($IRES_{CP}$).

10. The process according to claim 7, wherein said protein of interest is selected from the group consisting of selectable markers, toxins, hormones, proteases and viral proteins.

11. The process according to claim 7, wherein said selectable marker confers antibiotic resistance or herbicide resistance.

12. The process according to claim 7, wherein the transcriptional promoter is a constitutive or inducible plant-specific promoter.

13. The process according to claim 7, wherein the recombinant DNA molecule additionally comprises at a 3' position of said second plant-expressible gene an IRES, which may be the same or different, and an additional gene encoding a desired polypeptide.

14. The process according to claim 7, wherein said process provides for coordinated expression of multiple polypeptides or several enzymes of a biosynthetic pathway.

15. The process according to claim 7, wherein said IRES is derived from a crucifer-infecting tobamovirus (crTMV).

* * * * *

SEQUENCE LISTING

<160> NUMBER OF SEQ ID NOS: 7

<210> SEQ ID NO 1
<211> LENGTH: 231
<212> TYPE: RNA
<213> ORGANISM: Tobacco mosaic virus, crucifer-infecting

<400> SEQUENCE: 1
aucuaaguua gguuguaaac auauuagaga cguuguucau uuggaagagu uacgcgaguc 60
uuugugugau guagcuagua accuaaauaa uugugcguau uuuucacagu uagaugaggc 120
cguugccgag guucauaaga ccgcgguagg cgguucguuu gcuuuuugua guauaauuaa 180
auauuuguca gauaagagau uguuuagaga uuuguucuuu guuugauaau g 231

<210> SEQ ID NO 2
<211> LENGTH: 231
<212> TYPE: RNA
<213> ORGANISM: Tobacco mosaic virus UI

<400> SEQUENCE: 2
guugaucucg aaacuuuggu gcuaaacaca ucaaggauug ggaacacuug gaggaguuca 60
gaaggucucu uugugauguu gcuguuucgu ugaacaauug ugcguauuac acacaguugg 120
acgacgcugu augggagguu cauaagaccg ccccuccagg uucguuuguu uauaaaaguc 180
uggugaagua uuugucugau aaaguucuuu uuagaaguuu guuuauagau g 231

<210> SEQ ID NO 3
<211> LENGTH: 78
<212> TYPE: RNA
<213> ORGANISM: Tobacco mosaic virus, crucifer-infecting

<400> SEQUENCE: 3
uucguuugcu uuuuguagua uaauuaaaua uuugucagau aagagauugu uuagagauuu 60
guucuuuguu ugauaaug 78

<210> SEQ ID NO 4
<211> LENGTH: 78
<212> TYPE: RNA
<213> ORGANISM: Tobacco mosaic virus UI

<400> SEQUENCE: 4
cuccagguuc guuuguuuau aaaagucugg ugaaguauuu gucugauaaa guucuuuuua 60
gaaguuuguu uauagaug 78

<210> SEQ ID NO 5
<211> LENGTH: 151
<212> TYPE: RNA
<213> ORGANISM: Tobacco mosaic virus, crucifer-infecting

<400> SEQUENCE: 5
gaauucgucg auucgguugc agcauuuaaa gcgguugaca acuuuaaaag aaggaaaaag 60
aagguugaag aaaagggugu aguaaguaag uauaaguaca gaccggagaa guacgccggu 120
ccugauucgu uuaauuugaa agaagaaaau g 151

<210> SEQ ID NO 6
<211> LENGTH: 151
<212> TYPE: RNA
<213> ORGANISM: Tobacco mosaic virus UI -continued

```
<400> SEQUENCE: 6
gcaaagggaa aaauaguagu aaugaucggu cagugccgaa caagaacuau agaaauguua     60
aggauuuugg aggaaugagu uuuaaaaaga auaauuuaau cgaugaugau ucggaggcua    120
cugucgccga aucggauucg uuuuaaauau g                                   151

<210> SEQ ID NO 7
<211> LENGTH: 231
<212> TYPE: RNA
<213> ORGANISM: Cucumber green mottle mosaic virus

<400> SEQUENCE: 7
agguaauaag agucuagaaa guuacgacca uuuagaggaa uuuagaauuu cucugaugga     60
cguggcaaaa ccuuuguuua augccgcuua uuuucaccuu uuagaugaug cuauccacga    120
guauuuuccu agcguagggg guagcaguuu ugcuauuaau ucuuugugca aguaccuuag    180
ugauaagugg uuguucaggu cucuuuuugc gaagucuucu gucuagauau g             231
```